United States Patent [19]

Chan

[11] 4,097,526
[45] Jun. 27, 1978

[54] PREPARATION OF ORGANIC SULFONE COMPOUNDS

[75] Inventor: John Kai-Fai Chan, Charleston, W. Va.

[73] Assignee: Union Carbide Corporation, New York, N.Y.

[21] Appl. No.: 767,487

[22] Filed: Feb. 10, 1977

[51] Int. Cl.$^2$ ............................................. C07C 131/00
[52] U.S. Cl. ........................... 260/566 AC; 260/465 E; 260/465.5 R; 260/453 RW; 260/558 S; 260/561 A; 260/566 A; 260/607 AR; 260/607 AL; 260/607 E; 560/12; 560/13
[58] Field of Search ........ 260/566 A, 566 AC, 465 E, 260/465.5 R, 453 RW, 558 S, 561 A, 607 AR, 607 AL, 607 E; 560/12, 13

[56] References Cited
FOREIGN PATENT DOCUMENTS
2,436,817  2/1976  Germany.

OTHER PUBLICATIONS
Wagner & Zook, "Synthetic Organic Chemistry" pp. 801–806, (1953).
Swern, Chemical Reviews, vol. 45, pp. 33–35 (1949).

*Primary Examiner*—Gerald A. Schwartz
*Attorney, Agent, or Firm*—Richard C. Stewart

[57] ABSTRACT

An in-situ process for preparing organic sulfone compounds by oxidizing the corresponding sulfide compound with a mixture of hydrogen peroxide, a carboxylic acid in the presence of a catalytic amount of a mineral acid or an organic sulfonic acid.

27 Claims, No Drawings

PREPARATION OF ORGANIC SULFONE COMPOUNDS

BACKGROUND OF THE INVENTION

This invention relates to a process for preparing organic sulfone compounds. More particularly, this invention relates to an improved process for oxidizing organic sulfide compounds in a relatively simple and efficient manner to the corresponding organic sulfone compound.

Organic sulfone compounds as well as oxidation processes for their preparation are well known in the art. Heretofore, organic sulfone compounds generally have been prepared by one of two oxidation processes which employ a peracid as the oxidizing agent. One process, the so-called "generator process", involves separately generating an anhydrous peracid oxidizing agent to be used for the oxidation of the organic sulfide compound at some later time. The other process, the so-called "in-situ" process is a one-step process which calls for the generation of the peracid oxidizing agent in-situ in the presence of the organic sulfide compound sought to be oxidized. Although they are relatively simple and efficient, both known processes suffer from a number of inherent disadvantages. For example, it is generally recognized that both of the previously disclosed peracid oxidation processes usually give rise to organic sulfone compounds that are contaminated with unacceptably large amounts of the corresponding sulfoxide compound as a by-product. This makes it necessary to carry out elaborate and cumbersome purification procedures which result in relatively small yields of the sulfone product. In addition, the generator process suffers from a further disadvantage in that it requires the generation and handling of the generally unstable and potentially hazardous anhydrous peracid. The conventional "in-situ" process, although simple and safe to operate, generally requires expensive high boiling reaction solvents, extended reaction periods, and high reaction temperatures with concomitant increased probability of thermal degradation products. Consequently, there exists a need for a more effective process for converting organic sulfide compounds in organic sulfone compounds with enhanced sulfone yields coupled with lower reaction temperatures and shorter reaction periods.

SUMMARY OF THE INVENTION

According to the present invention there is provided an improved process for preparing organic sulfone compounds by reacting the corresponding organic sulfide compound with a mixture of hydrogen peroxide and a carboxylic acid, the improvement which comprises conducting the reaction in the presence of a catalytically effective amount of a mineral acid or an organic sulfonic acid.

It has been found that the oxidizing agent employed in the process of this invention not only provides excellent conversion activity under mild reaction conditions but at the same time exhibits superior selectivity in the oxidation of the sulfide linkage to the exclusion of other oxidizable moieties that may be present in the molecule. The process of this invention is extremely valuable in that it provides a high yield of a high quality organic sulfone compound which is relatively free of sulfoxide contaminants and other reaction by-products, while at the same time employing mild reaction conditions, short reaction periods and low reaction temperatures.

DESCRIPTION OF THE PREFERRED EMBODIMENTS

The organic sulfide compounds that can be employed as reactants in the process of this invention include cyclic or linear, aliphatic or aromatic organic compounds containing one or more divalent sulfur groups. Suitable organic sulfide compounds will contain carbon and hydrogen with oxygen and nitrogen as optional components. The carbon atoms can be acyclic or cyclic; saturated and/or unsaturated such as aliphatic, cycloaliphatic bicycloaliphatic, aromatic (including fused and bridged carbon atoms) and the like. The nitrogen components may be in the form of imino; amino; nitrilo; or nitro groups and the like. The oxygen containing components can be groups such as hydroxyl, either aliphatic or phenolic; carboxyl; carbonyloxy; etheroxy; or carbonyl groups or the like. The organic sulfide compound may be substituted with one or more substituents such as chlorine, fluorine, bromine, iodine and the like, the only requirement being that the substituent be unreactive with the peracid unless multiple oxidations are desired.

Preferred organic sulfide reactants are those of the formula:

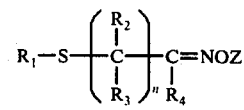

wherein:
$n$ is 0 to 5;
$R_1$ is alkyl, phenyl, phenylalkyl, alkenyl, alkynyl, cycloalkyl or cycloalkenyl all of which may be substituted with one or more chloro, fluoro, bromo, cyano, nitro, alkyl, alkoxy, alkylthio, alkylsulfinyl, alkylsulfonyl, or alkoxyalkyl;
$R_2$ and $R_3$ are individually hydrogen or either substituted or unsubstituted alkyl wherein the permissible substituents are one or more chloro, fluoro, bromo, cyano, nitro or alkoxy;
$R_4$ is hydrogen, chloro, fluoro, bromo, cyano, alkyl, alkylsulfonyl, alkoxy, alkylthio, alkylsulfinyl, alkoxy, carbonalkoxy, alkylsulfonyl, alkoxyalkyl, alkylthioalkyl, alkylsulfonylalkyl or alkylsulfinylalkyl, in which any alkyl moiety may be substituted with one or more chloro, bromo, fluoro, cyano, amido or nitro;
Z is hydrogen or

wherein: $R_5$ and $R_6$ are individually hydrogen or either substituted or unsubstituted alkyl, phenyl or phenylalkyl wherein the permissible substituents are one or more chloro, fluoro, bromo, nitro, cyano, alkyl or alkoxy.

Illustrative of suitable organic sulfide reactants are:
2-Acetylamino-4-methyl-4-nitro-5-thiazolylphenyl sulfide,
4-Aminodiphenyl sulfide,
Benzyl carboxymethyl sulfide,
1,2-Bis(2-benzoxyethylmercapto)ethane,
1,2-Bis(2-hydroxyethylmercapto)ethane,
Bis(4-nitro-1-naphthyl)sulfide,
2-Bromo-8-nitrothiazanthene, Isobutyl 2-chloroethyl sulfide,
n-Butyl p-tolyl sulfide,
4'-Chloro-4-aminodiphenyl sulfide,
2-Chloroethyl p-tolyl sulfide,
2-Chloro-2'-methylthiodiethyl sulfide,
1-Chlorovinyl 2-chloroethyl sulfide,
2-Crotonyl-4'-nitro-5-thiazolyphenyl sulfide,
Diphenylmethyl a-naphthyl sulfide,
Diphenylmethyl phenyl sulfide,
Di(p-tolyl) sulfide,
Divinyl sulfide,
Ethyl n-butyl sulfide,
Ethyl ethoxymethyl sulfide,
Ethylene-sulfur chloride reaction product,
Ethyl oleyl sulfide,
4-(2-Hydroxyethylthio)-2-aminobutyric acid,
2-Hydroxyethyl naphthenyl sulfides,
4-Iodo-4'-nitrodiphenyl sulfide,
6-Methoxy-8-(4-quinazolonyl)phenyl sulfide,
Allyl benzyl sulfide,
2-Methylthiopropionaldehyde N-methylcarbamoyloxime,
2-Ethylthiopropionaldehyde N-methylcarbamoyloxime,
2-n-Propylthiopropionaldehyde N-methylcarbamoyloxime,
2-Isopropylthiopropionaldehyde N-methylcarbamoyloxime,
2-n-Butylthiopropionaldehyde N-methylcarbamoyloxime,
2-sec-Butylthiopropionaldehyde N-methylcarbamoyloxime,
2-t-Butylthiopropionaldehyde N-methylcarbamoyloxime,
2-Isobutylthiopropionaldehyde N-methylcarbamoyloxime,
2-Heptylthiopropionaldehyde N-methylcarbamoyloxime,
2-Decylthiopropionaldehyde N-methylcarbamoyloxime,
2-Vinylthiopropionaldehyde N-methylcarbamoyloxime,
2-(2-Propenylthio)propionaldehyde N-methylcarbamoyloxime,
2-(3-Butenylthio)propionaldehyde N-methylcarbamoyloxime,
2-Hexenylthiopropionaldehyde N-methylcarbamoyloxime,
2-Ethynylthiopropionaldehyde N-methylcarbamoyloxime,
2-Phenylthiopropionaldehyde N-methylcarbamoyloxime,
2-(α-Naphthylthio)propionaldehyde N-methylcarbamoyloxime,
2-Benzylthiopropionaldehyde N-methylcarbamoyloxime,
2-(4-Chlorophenylthio)propionaldehyde N-methylcarbamoyloxime,
2-(2,4-Dichlorophenylthio)propionaldehyde N-methylcarbamoyloxime,
2-Methyl-2-methylthiopropionaldehyde N-methylcarbamoyloxime,
2-Methyl-2-ethylthiopropionaldehyde N-methylcarbamoyloxime,
2-Methyl-2-n-Propylthiopropionaldehyde N-methylcarbamoyloxime,
2-Methyl-2-isopropylthiopropionaldehyde N-methylcarbamoyloxime,
2-Methyl-2-butylthiopropionaldehyde N-methylcarbamoyloxime,
2-Methyl-2-heptylthiopropionaldehyde N-methylcarbamoyloxime,
2-Methyl-2-decylthiopropionaldehyde N-methylcarbamoyloxime,
2-Methyl-2-vinylthiopropionaldehyde N-methylcarbamoyloxime,
2-Methyl-2-(2-propenylthio)propionaldehyde N-methylcarbamoyloxime,
2-Methyl-2-(3-butenylthio)propionaldehyde N-methylcarbamoyloxime,
2-Methyl-2-hexenylthiopropionaldehyde N-methylcarbamoyloxime,
2-Methyl-2-ethynylthiopropionaldehyde N-methylcarbamoyloxime,
2-Methyl-2-phenylthiopropionaldehyde N-methylcarbamoyloxime,
2-Methyl-2-(α-napthylthio)propionaldehyde N-methylcarbamoyloxime, 2-Methyl-2-benzylthiopropionaldehyde N-methylcarbamoyloxime,
2-Methyl-2-(2-chlorophenylthio)propionaldehyde N-methylcarbamoyloxime,
2-Methyl-2-(4-chlorophenylthio)propionaldehyde N-methylcarbamoyloxime,
2-Methyl-2-(2,4-dichlorophenylthio)propionaldehyde N-methylcarbamoyloxime,
2-Methylthiobutyraldehyde N-methylcarbamoyloxime,
2-Methylthiopentanaldehyde N-methylcarbamoyloxime,
2-Methylthiohexanaldehyde N-methylcarbamoyloxime,
2-Methylthioheptanaldehyde N-methylcarbamoyloxime,
2-Methylthiodecanaldehyde N-methylcarbamoyloxime,
2-Methyl-2-methylthiobutyraldehyde N-methylcarbamoyloxime,
2-Ethyl-2-methylthiobutyraldehyde N-methylcarbamoyloxime,
2-Butyl-2-methylthioheptanaldehyde N-methylcarbamoyloxime,
2-Octyl-2-methylthiodecanaldehyde N-methylcarbamoyloxime,
2-[O-(Methylcarbamoyl)oximino]-33-dialkyl-1,4-dithiane,
3-[O-(Methylcarbamoyl)oximino]-2,2-dialkylthiolane,
2-(Ethylthiomethyl)phenyl methylcarbamate,
2,4,5-Trichlorophenyl 4-chlorophenyl sulfide,
4-Chlorophenyl phenyl sulfide,
3,5-Dimethyl-4-(methylthio)-phenyl methylcarbamate
Bis[4-(methylcarbamoyloxy)phenyl] sulfide
2-Methyl-3-(phenylcarbamoyl)-5,6-dihydro-1,4-oxathin.
3-[O-(Methylcarbamoyl)oximino]-2,2-dialkylthiane Carboxylic acids useful in the conduct of the process of this invention are well known to those skilled in the synthetic art and will correspond to the following generic formula:

wherein R is either substituted or unsubstituted aromatic or aliphatic group such as alkyl, aryl, arylalkyl or alkylaryl group. Permissible substituents include but are not limited to halogen, cyano, nitro or the like. Illustrative of carboxylic acids useful in the conduct of the process of this invention are benzoic acid, p-chlorophenoxyacetic acid, acetic acid, butanoic acid, heptanoic acid, formic acid, p-methoxybenzoic acid, toluic acid, valeric acid, propionic acid, B-naphthoic acid, 4-(1-naphthyl)-4-butanoic acid, 3-(2-naphthyl)butyric acid or the like. In general to achieve acceptable results it is necessary to employ at least one mole of carboxylic acid per equivalent of the divalent sulfide functional unit present in the organic sulfide compound. The preferred amount of carboxylic acid employed is from about 1 to about 4 moles of acid per equivalent sulfide functional unit present in the sulfide reactant. The particularly preferred amount of carboxylic acid employed is from about 1.5 to about 2.0 moles per mole of sulfide functional unit. In order to achieve a satisfactory conversion of the sulfide compound to the sulfone compound an excess of hydrogen peroxide should be employed. The preferred amount of hydrogen peroxide is from about 2 to about 5 moles of hydrogen peroxide per equivalent of sulfide functional unit present in the sulfide reactant. The particularly preferred amount of hydrogen peroxide is from about 2.3 to about 2.0 moles per mole of sulfide function unit.

The process of this invention is always conducted in the presence of an acid catalyst. In general any conventional mineral acid or organic sulfonic acid may be used. Illustrative of suitable mineral acid that can be employed in the conduct of the process of this invention are phosphoric acid, nitric acid, sulfuric acid, hydrochloric acid, boric acid, perchloric acid, hypochloric acid and the like. Illustrative of useful organic sulfonic acids are benzenesulfonic acid, p-toluenesulfonic acid, p-nitrobenzenesulfonic acid, 2-naphthalensulfonic acid and the like.

The quantity of acid catalyst employed in conduct of the process of this invention can be varied over a wide range. In general, the reaction proceeds satisfactory when employing as little as about 0.010 weight percent of the acid catalyst based on the quantity of the reactants. The upper concentration limit can be quite high, as for example about 10.0 weight percent, and higher. In the preferred embodiment of this process, an acid catalyst concentration of from about 0.10 to about 7.0 weight percent based on quantity of the reactants is useful.

The reaction temperature is not critical and can be varied over a wide range. The process is normally conducted at a temperature in the range of from about 0° C. and upwards to approximately 120° C. Preferred reaction temperatures are from about 25° to about 75° C. At temperatures below 25° C. the rate of reaction becomes markedly slower, while at temperatures above 75° C. product degradation may occur.

The process can be carried out neat or in solution. A normally liquid organic solvent is preferably employed as the reaction medium. In general any organic solvent inert to oxidation by mild oxidative agents may be used. Illustrative of the organic solvents which are suitable as reaction solvents in the practice of the preferred embodiments of this invention are saturated and unsaturated aliphatic and aromatic hydrocarbons, e.g. hexane, cyclohexane, octane, dodecane, naphtha, decalin, kerosene, tetrahydronapthalene, cycloheptane, alkylcycloalkane, benzene, toluene, xylene, naphthalene, alkyl napthalene, or the like; ethers such as tetrahydrofuran, tetrahydropyran, diethyl ether, dioxane, 1,2-methyoxybenzene, 1,2-ethoxybenzene, the mono and dialkyl ethers of ethylene glycol, of dipropylene glycol, of butylene glycol, of diethylene glycol, of dipropylene glycol. Preferred solvents for the conduct of the process of this invention are chlorinated aliphatic hydrocarbons as for example, chloroform, methylene dichloride, 1,1-dichloroethane, carbon tetrachloride or the like.

Reaction pressures are not critical. The process of this invention can be conducted at either subatmospheric, atmospheric or superatmospheric pressure. For convenience, the reaction is usually conducted at atmospheric or autogenous pressure.

The process of this invention is effected over a period of time sufficient to produce the desired organic sulfone compound. In general, residence times can vary from a few minutes to approximately 24 hours or longer. In most instances, when employing preferred reaction conditions, reaction times will be found to vary from about 2 hours to about 4 hours. Reaction time is influenced to a significant degree by the reaction temperature, the concentration and choice of acid catalyst, the choice and concentration of diluent and other factors known to those skilled in the synthetic art.

The process of this invention can be conducted in a batch, semicontinuous or continuous fashion. The reaction can be conducted in a single reaction zone or in a plurality of reaction zones, in series or in parallel or it may be conducted intermittently or continuously in an elongated tubular zone or series of such zones. The materials of construction employed should be inert to the reactants during the reaction and the fabrication of the equipment should be able to withstand the reaction temperatures and pressure.

The process is preferably conducted in either glass lined, stainless steel 316 or Hastelloy C-276 reaction equipment. The reaction zone can be fitted with one or more internal and/or external heat exchanger(s) in order to control undue temperature fluctuations, or to prevent any possible "runaway" reaction temperatures. In preferred embodiments of the process, agitation means to vary the degree of mixing the reactions mixture can be employed. Mixing by vibration, shaking, stirring, rotation, oscillation, ultrasonic vibration or the like are all illustrative of the types of agitation means contemplated. Such means are available and well known to those skilled in the art.

The acid catalyst may be initially introduced into the reaction zone batchwise or it may be continuously or intermittently introduced in such zone during the course of the proces. Means to introduce and/or adjust the quantity of reactants introduced, either intermittently or continuously into the reaction zone during the course of the reaction can be conveniently utilized in the process especially to maintain the desired molar ratio of the solvent and reactants.

In accordance with the preferred embodiments of the process of this invention, an organic sulfide compound is treated with an aqueous mixture of hydrogen peroxide, a carboxylic acid, and a catalytic amount of a mineral acid or an organic sulfonic acid in a suitable reaction solvent. The manner and order in which the reaction components are mixed is not critical. In general, the organic sulfide reactant carboxylic acid and a suitable reaction solvent are placed in a suitable reaction vessel and hydrogen peroxide and the acid catalysts are added in consecutive order, preferably with moderate agitation and the reaction mass heated to the desired temperature.

One preferred and representative embodiment of the process of this invention involves adding an aqueous solution of hydrogen peroxide to a mixture of an organic sulfide compound and formic acid in a chlorinated aliphatic hydrocarbon under ambient conditions. After the additions, either sulfuric, phosphoric or p-toluenesulfonic acid either in the form of a concentrated solution or as a 50 percent aqueous solution is then added followed by refluxing at temperature of about 50° C. The reaction product can be isolated employing standard processing equipment and conventional isolation techniques as for example distillation, crystalization, decantation or the like.

The manner of practicing the process of the present invention and advantages obtained thereby will be illustrated by the following specific examples which are merely illustrative and are not intended, in any manner, to limit the scope of the invention.

EXAMPLE I

Procedure 55 grams of a 30 percent aqueous hydrogen peroxide solution was added dropwise to a mixture of 55 grams of 2-methyl-2-(methylthio)propionaldehyde O-(methylcarbamoyl)oxime and 15 grams of formic acid in 200 grams of methylene chloride solution over a 15-20 minute period. The temperature rose from 25° to 40° C. during the addition. When the addition was complete 3 grams of concentrated sulfuric acid was added dropwise to maintain a gentle reflux followed by an additional 2 hours of reflux at 40°-45° C. After the reaction period was over, methylene chloride solvent was evaporated under reduced pressure. The mixture was cooled to 5° C. and filtered. The 2-methyl-2-(methylsulfonyl)-propionaldehyde solid obtained was washed with 200 ml of water and dried to give 37 grams 2-methyl-2-(methylsulfonyl)propionaldehyde O-(methylcarbamoyl)oxime m.p. 145°-147° C. The yield was 90.5 percent based on 2-methyl-2-(methylthio)propionaldehyde.

The product was found to contain 0.05 weight percent of 2-methyl-2-(methylsulfinyl)propionaldehyde O-(methylcarbamoyl)oxime (sulfoxide) by liquid-liquid chromatographic analysis.

EXAMPLE II

Procedure 15 grams of an 88 percent aqueous solution of formic acid was added to a mixture containing 30 grams of 2-methyl-2-(methylthio)propionaldehyde O-(methylcarbamoyl)oxime in 70 grams of methylene chloride solution. To the mixture was added 56 grams of a 30 percent aqueous hydrogen peroxide over a 15-20 minute period. During the course of addition, the reaction temperature rose from 25° to 40° C. with a gentle reflux of methylene chloride. After the addition of the peroxide solution, 6.0 grams of concentrated sulfuric acid was added dropwise at a rate to maintain the reflux at 40° C. When the addition was complete, the mixture was stirred for an additional 2.5 hours at 40.45° C. When the oxidation was over, 60-70 grams of the methylene chloride solvent was removed by evaporation under reduced pressure. The mixture was cooled to 5° C. and filtered. The solid reaction product was then washed with 25-30 grams of cold water and dried to constant weight. (2-Methyl-2-(Methylsulfonyl)propionaldehyde O-(methylcarbamoyl)oxime was obtained, m.p. 144°-145° C, having a 2-methyl-2-(methylsulfinyl)propionaldehyde O-(methylcarbamoyloxime (sulfide) content of less than 0.10 percent.

EXAMPLE III

Procedure

The reaction of EXAMPLE I was repeated using 3.0 grams of phosphoric acid instead of sulfuric acid, as the catalyst, the reaction conditions and recovery procedure being otherwise the same. The 2-methyl-2-(methylsulfonyl)propionaldehyde O-(methylcarbamoyl)oxime product obtained was 27.7 grams, representing a 79 percent yield based on 2-methyl-2-(methylthio)propionaldehyde O-(methylcarbamoyl)oxime. The product had a 2-methyl-2-(methylsulfinyl)propionaldehyde O-(methylcarbamoyl)oxime (sulfoxide) content of 1.95%.

EXAMPLE IV

Procedure

The reaction of EXAMPLE I was repeated with 4.0 grams of p-toluenesulfonic acid as catalyst and a reaction contact time of 5 hours. The reaction conditions and recovery procedure otherwise being the same. The 2-methyl-2-(methylsulfonyl)propionaldehyde O-(methylcarbamoyl)oxime reaction product obtained was 23.0 grams, representing a 66 percent yield based on 2-methyl-2-(methylthio)propionaldehyde O-(methylcarbamoyl)-oxime reactant. The reaction product had a 2-methyl-2-(methylsulfinyl)propionaldehyde O-(methylcarbamoyl)oxime (sulfoxide) content of less than 0.1%.

EXAMPLE V

Procedure

The reaction of EXAMPLE I was repeated with 3.0 grams of phosphoric acid as catalyst. The reaction conditions and recovery procedure otherwise being the same. The 2-methyl-2-(methylsulfonyl)-propionaldehyde O-(methylcarbamoyl)oxime obtained was 27.5 grams representing a 77 percent yield based on 2-methyl-2-(methylthio)-propionaldehyde O-(methylcarbamoyl)oxime. The reaction product had a 2-methyl-2-(methylsulfinyl)-propionaldehyde O-(methylcarbamoyl)oxime (sulfoxide) content of less than .10%.

EXAMPLE VI

Procedure

Formic acid (88 percent, 4.5 grams) was added to a mixture containing 10 grams of 3,3-dimethyl-1-(methylthio)-2-butanone O-(methylcarbamoyl)oxime in 30 grams of methylene chloride solution. To the mixture was added 16.5 grams of a 30-percent aqueous hydrogen peroxide over a 20-30 minute period. During addition the reaction temperature rose from 25° to 35° C. When the addition was complete, a mixture containing 1 gram of concentrated sulfuric acid and 1 gram of water was added dropwise to the reaction mixture and the mixture was then refluxed at 40°-42° C. for 2 hours. After reflux about 75 grams of methylene chloride was added to dilute the mixture and the organic layer was separated by decantation. The organic layer was washed once with water and then evaporated to dryness under reduced pressure. A total of 11 grams of a residual product was obtained which was identified by spectral analysis as 3,3-dimethyl-1-(methylsulfonyl)-2-butanone O-(methylcarbamoyl)oxime. The yield was 95.9 percent. The product had a 3,3-dimethyl-1-(methylsulfinyl-2-butanone O-(methylcarbamoyl)oxime (sulfoxide) content of less than 0.10%.

EXAMPLE VII

Procedure

Employing the same reaction conditions as described in EXAMPLE VI, 56 grams of 30 percent aqueous hydrogen peroxide was added to a mixture of 15 grams of 88 percent formic acid and 30 grams of phenyl sulfide in 70 parts of methylene chloride solvent, followed by the addition of 4 grams of concentrated sulfuric acid. The reaction mixture was refluxed for two-hours at 40°–44° C. A total of 31 grams of the (bis)-phenylsulfone product was obtained, representing a 88.4% yield. The product was identified as the desired sulfone by melting point and by spectral analyses. The reaction product had a phenyl sulfoxide content of less than 0.10%.

The reactions of Examples VIII–XVI were con-

EXAMPLE XVII

Procedure 56 grams of a 30 percent aqueous hydrogen peroxide solution was added dropwise to a mixture of 30 grams of 2-methyl-2-(methylthio)propionaldehyde O-(methylcarbamoyl and 15 grams of an 80% aqueous formic acid solution in 70 grams of methylene chloride. After the addition the reaction mixture was refluxed for 2 hours at a temperature of 40°–45° C. The methylene chloride solvent was then evaporated under reduced pressure and the reaction mixture was then cooled to 5° C. and filtered. The 2-methyl-2-(methylsulfonyl)propionaldehyde O-(methylcarbamoyl)oxime reaction product, m.p. 137°–138° C., obtained was 12.6 grams which represented a 34 percent yield. The reaction product had a 2-methyl-2-(methylsulfinyl)propionaldehyde O-(methylcarbamoyl)oxime (sulfoxide) content of 15.28 percent.

TABLE II

| | | COMPARISON DATA | | | |
|---|---|---|---|---|---|
| EXAMPLE | grams of 88% Aqueous Formic Acid | grams of 30% Aqueous $H_2O_2$ Solution | grams of Acid Catalyst | grams of Sulfone Product | Percent Yield of Sulfone Product | Sulfoxide Content |
| I | 15 | 56 | 3.0g of $H_2SO_4$ | 28.0 | 80 | 0.05% |
| IV | 15 | 56 | 4.0g of (p-$CH_3C_6H_4SO_3H$) | 23.0 | 66 | 0.1% |
| V | 15 | 56 | 3.0g of $H_3PO_4$ | 27.5 | 77 | 0.1% |
| XVIII | 15 | 56 | 0g of Acid | 12.69 | 34 | 15.28% | ducted utilizing the procedure of EXAMPLES I–VII. In each of these Examples, 100 grams of a 30 percent 2-methyl-2-(methylthio)propionaldehyde O-(methylcarbamoyl)oxime methylene chloride solution, an 88 percent aqueous formic acid solution and a 30% aqueous hydrogen peroxide solution were used as the starting materials. The contact time was 2.5 hours at a temperature of 40°–43° C. 2-(Methyl-2-(methylsulfonyl)-propionaldehyde O-(methylcarbamoyl)oxime (sulfone) was obtained as one crop, whose 2-methyl-2-(methylsulfinyl)propionaldehyde O-(methylcarbamoyl)oxime (sulfoxide) content was determined by the liquid-liquid chromatographic technique. The results of EXAMPLES VIII–XVI are set forth in TABLE I below:

The data presented in TABLE II hereinabove clearly illustrates the greatly increased efficiency of the peracid oxidation process of this invention in comparison with known peracid oxidation processes. For example, the known process of EXAMPLE XVIII which was conducted without a mineral acid or a sulfonic acid catalyst had a 34% yield of the organic sulfone product which contaminated with 15.28% sulfoxide by-product. This results is to be contrasted with EXAMPLES I, IV and V which employ the process of this invention. Note that the sulfone product of EXAMPLES I, IV and V was produced in an 80%, 66% and 77% yield, respectively. Further, EXAMPLES I, IV and V which were conducted with an acid catalyst yield an organic sulfone

TABLE I

| ACID CATALYZED "IN-SITU" OXIDATION PROCESS | | | | | |
|---|---|---|---|---|---|
| EXAMPLE | grams of 88% Formic Acid | grams of 30% $H_2O_2$ Solution | grams of Acid Catalyst | Sulfone Product | Yield Percent Sulfone | Sulfoxide Content |
| VIII | 15g | 56g | 1.0g($H_2SO_4$) | 21.0g | 61 | 8.24% |
| IX | 15g | 56g | 2.0g($H_2SO_4$) | 27.0g | 77 | 2.35% |
| X | 15g | 40g | 2.0g($H_2SO_4$) | 26.0g | 74 | 3.59% |
| XI | 15g | 56g | 4.0g($H_2SO_4$) | 28.5g | 81 | 0.1% |
| XII | 15g | 56g | 9.0g($H_2SO_4$) | 27.1g | 77 | 0.1% |
| XIII | 12g | 56g | 3.0g($H_2SO_4$) | 29.2g | 83 | 0.1% |
| XIV | 10g | 56g | 3.0g($H_2SO_4$) | 28.6g | 82 | 0.1% |
| XV | 15g | 65g | 4.0g($H_2SO_4$) | 26.3g | 75 | 0.1% |
| XVI | 12g | 56g | 4.0g(p-$CH_3C_6H_4SO_3H$) | 23.0g | 66 | 0.1% |

To more particularly demonstrate the increased efficiency of the peracid oxidation process of this invention in comparison with known peracid oxidation processes, the experimental results of three representative examples of the process of this invention were compared with the experimental results from an example of a known process. The comparison data is set forth in TABLE II hereinbelow. The known peracid oxidation process was conducted as described in EXAMPLE XVII below.

product which was contaminated with only 0.10% of the sulfone by-product. This represents over a two-fold increase in the % yield of the sulfone and a 152.8 fold decrease in the degree of sulfoxide by-product contamination.

The organic sulfone compounds prepared in accordance with the process of this invention have wide utility and are valuable for a number of useful purposes. Some of the organic sulfone compound prepared in accordance with the process of the inventions exhibited outstanding insecticidal, nematocidal and miticidal activity and may be utilized as insecticides, miticides and nematocides according to methods known to those skilled in the pesticidal art. These compounds are also relatively non-toxic to plants and mammals when used in amounts sufficient to kill insects, mites and nematodes. Thus, for example, 2-methyl-2-(methylsulfonyl)-propionaldehyde O-(methylcarbamoyl)oxime an outstanding pesticide may be conveniently prepared by the process of this invention. It should be pointed out, however, that other organic sulfone compounds prepared by the process of this invention are not limited to use as pesticides but in addition are extremely useful for other purposes which are known to those skilled in the art.

Various modifications and variations of this invention will be obvious to a worker skilled in the art and it is to be understood that such modifications are to be included within the purview of this application and the spirit and scope of the appended claims.

What is claimed is:

1. In a process for oxidizing an organic sulfide compound to its corresponding sulfone compound with a mixture of hydrogen peroxide and a carboxylic acid, the improvement which comprises conducting the reaction in the presence of a catalytically effective amount of a mineral or an organic sulfonic acid.

2. A process according to claim 1 wherein said acid catalyst is a mineral acid.

3. A process according to claim 1 wherein said acid catalyst is an organic sulfonic acid.

4. A process according to claim 1 wherein said acid catalyst is selected from the group consisting of sulfuric acid, nitric acid, perchloric acid, hydrochloric acid or phosphoric acid.

5. A process according to claim 1, wherein said acid catalyst is selected from the group consisting of benzenesulfonic acid, toluenesulfonic acid, p-nitrobenzenesulfonic acid or 1-naphthalenesulfonic acid.

6. A process according to claim 1 which is conducted in the presence of from about 0.010 to about 10.0 weight percent of an acid catalyst based on the total weight of the reactants.

7. A process according to claim 1 which is conducted in the presence of from about 0.1 to about 7.0 weight percent of an acid catalyst based on the total weight of the reactants.

8. A process for preparing a compound of the formula:

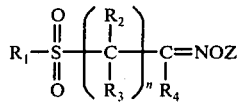

which comprises treating a compound of the formula:

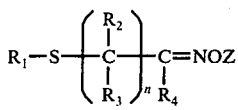

with a mixture of hydrogen peroxide and a carboxylic acid in the presence of a catalytically effective amount of a mineral or organic sulfonic acid, wherein:

$n$ is 0 to 10;

$R_1$ is alkyl, phenyl, phenylalkyl, alkenyl, alkynyl, cycloalkyl, or cycloalkenyl all of which may be substituted with one or more chloro, fluoro, bromo, cyano, nitro, alkyl, alkoxy, alkylsulfonyl or alkoxyalkyl groups;

$R_2$ and $R_3$ are individually hydrogen or either substituted or unsubstituted alkyl; wherein the permissible substituents are one or more chloro, fluoro, bromo, cyano, nitro or alkoxy substituents;

$R_4$ is hydrogen, chloro, fluoro, bromo, cyano, alkyl, alkylsulfonyl, alkoxy, carboalkoxyalkylsulfonyl, alkoxyalkyl or alkylsulfonylalkyl groups in which any alkyl moiety may be substituted with one or more chloro, bromo, fluoro, cyano, amido or nitro group;

Z is hydrogen or

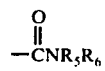

wherein:

$R_5$ and $R_6$ are individually hydrogen or either substituted or unsubstituted alkyl, phenyl or phenylalkyl wherein the permissible substituents are one or more chloro, fluoro, bromo, nitro, cyano, alkyl or alkoxy groups.

9. A process according to claim 8 wherein $R_1$ is alkyl.

10. A process according to claim 8 wherein $n$ is 0, 1 or 2.

11. A process according to claim 8 wherein $R_2$ and $R_3$ are individually hydrogen or alkyl having from 1 to 4 carbon atoms.

12. A process according to claim 8 wherein $R_4$ is hydrogen or alkyl having from 1 to 4 carbon atoms.

13. A process according to claim 8 wherein Z is hydrogen.

14. A process according to claim 8 wherein Z is

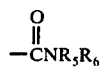

wherein:

$R_5$ and $R_6$ are individually hydrogen or alkyl.

15. A process according to claim 8 wherein said acid catalyst is a mineral acid.

16. A process according to claim 15 wherein said acid catalyst is selected from the group consisting of sulfuric acid, nitric acid, perchloric acid, hydrochloric acid or phosphoric acid.

17. A process according to claim 8 wherein said acid catalyst is an organic sulfonic acid.

18. A process according to claim 17 wherein said acid catalyst is selected from the group consisting of benzenesulfonic acid, toluenesulfonic acid, p-nitrobenzenesulfonic acid or 1-naphthalenesulfonic acid.

19. A process according to claim 8 which is conducted in the presence of from about 0.010 to about 10.00 weight percent of acid catalyst based on the total weight of the reactants.

20. A process according to claim 8 which is conducted in the presence of from about 0.10 to about 7.0 weight percent of acid catalyst based on the total weight of the reactants.

21. A process for preparing a compound of the formula:

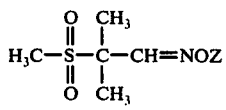

which comprises treating a compound of the formula:

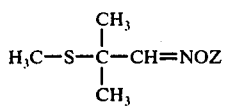

with a mixture of hydrogen peroxide and a carboxylic acid in the presence of a catalytically effective amount of a mineral or sulfonic acid, wherein:
Z is hydrogen or

22. A process according to claim 21 wherein said acid catalyst is a mineral acid.

23. A process according to claim 21 wherein said acid catalyst is an organic sulfonic acid.

24. A process according to claim 21 wherein said acid catalyst is selected from the group consisting of sulfuric acid, nitric acid, perchloric acid, hydrochloric acid or phosphoric acid.

25. A process according to claim 21 wherein said acid catalyst is selected from the group consisting of benzenesulfonic acid, toluenesulfonic acid, p-nitrobenzenesulfonic acid, 2-naphthalenesulfonic acid or 1-naphthalenesulfonic acid.

26. A process according to claim 21 which is conducted in the presence of from about 0.01 to about 10.0 weight percent of acid catalyst based on the total weight of the reactants.

27. A process according to claim 21 which is conducted in the presence of from about 0.1 to about 7 weight percent of acid catalyst based on the total weight of the reactants.

* * * * *